United States Patent [19]

Rosenthal

[11] Patent Number: 4,970,671

[45] Date of Patent: Nov. 13, 1990

[54] BIAS DRIFT COMPENSATION IN NEAR INFRARED QUANTITATIVE ANALYSIS INSTRUMENTS

[75] Inventor: Robert D. Rosenthal, Gaithersburg, Md.

[73] Assignee: Trebor Industries, Inc., Gaithersburg, Md.

[21] Appl. No.: 286,740

[22] Filed: Dec. 20, 1988

[51] Int. Cl.⁵ .............................................. G01D 18/00
[52] U.S. Cl. ................................ 364/571.05; 364/498; 250/252.1
[58] Field of Search .................... 364/571.05, 571.03, 364/557, 556, 498; 250/339, 341, 252.1 A

[56] References Cited

U.S. PATENT DOCUMENTS

| | | | |
|---|---|---|---|
| 3,681,577 | 8/1972 | Gasinus | 364/498 |
| 4,040,747 | 8/1977 | Webster | 364/525 |
| 4,171,913 | 10/1979 | Wildy et al. | 364/498 |
| 4,286,327 | 8/1981 | Rosenthal et al. | 364/498 |
| 4,404,642 | 9/1983 | Rosenthal | 364/571.03 |
| 4,687,934 | 8/1987 | Passaro et al. | 250/252.1 A |
| 4,744,657 | 5/1988 | Aralis et al. | 356/319 |

*Primary Examiner*—Gary Chin
*Assistant Examiner*—S. A. Melnick
*Attorney, Agent, or Firm*—Bernard, Rothwell & Brown

[57] ABSTRACT

The invention provides for the elimination of error due to bias shift in near infrared instrumentation having a plurality of near infrared sources. It accomplishes this by comparing subsequent Optical Density readings of a calibration standard for each near infrared source with stored calibration standard readings for each near infrared source that were taken when the instrument was initially calibrated, and compensating for any bias shift accordingly.

8 Claims, 5 Drawing Sheets

Initial calibration with standard

Calibration with standard after bias shift

BIAS DRIFT COMPENSATION IN NEAR INFRARED QUANTITATIVE ANALYSIS INSTRUMENTS

BACKGROUND OF THE INVENTION

1. Field of the Invention

The invention relates to improvements in near infrared quantitative analysis instruments.

2. Background of the Prior Art

Near infrared quantitative analysis instruments are known and commercially available. Such instruments as are known in the prior art make use of the phenomena that certain organic substances absorb energy in the near infrared (near-IR) region of the spectrum. In measuring the amount of energy absorbed by the substances at specific wavelengths (i.e., the Optical Density of the material) precise quantitative measurements of the constituents of the material can be determined. For example, protein, oil and moisture analyses of cereal grains can be determined by such instruments. For general introduction to near infrared quantitative analysis, see the paper presented by Robert D. Rosenthal to the 1977 Annual Meeting of American Association of Cereal Chemists, entitled "An Introduction to Near Infrared Quantitative Analysis".

Commonly owned U.S. Pat. Nos. 4,286,327 and 4,466,076 disclose near infrared instruments wherein the radiation source is a plurality of infrared emitting diodes (IREDs). In contrast to broad band light analytical instruments, IRED-type instruments are more subject to bias shift. The reason for this is that broad band light instruments generally have only a single illumination source, i.e., a light bulb, and if the illumination source changes intensity, it usually affects all emitted wavelengths identically. Thus, a change in intensity of the single light bulb does not cause bias shift of the instrument. In an IRED-type instrument with multiple IREDs, this "self compensating" effect of having a single light source does not exist. Thus, if any single IRED changes intensity, the result is an apparent absorbance that differs from the true absorbance of the sample being tested. This absorbance shift can be caused by shifts in the IRED center wavelength and changes in the IRED half-power band width. These may result from IRED temperature changes related to changes in intensity. Another source of error in IRED instruments may result from changes in the optical filters used. For example, if an optical filter changes in its band width or center wavelength, it can cause an IRED-type instrument to have a bias shift.

There thus remains a need in the art for near infrared quantitative analysis instruments that provide for reduction or elimination of error due to bias shift.

SUMMARY OF THE INVENTION

The present invention provides a method and apparatus for near infrared quantitative analysis which is corrected for bias shift. A plurality of near infrared emitting sources are provided for transmitting near infrared energy through a sample, and a sensor is provided for detecting near infrared energy transmitted through the sample and for supplying a signal corresponding to the Optical Density of the sample for each of the near infrared sources. A computer is provided that stores individual initial Optical Density values of a calibration standard for each of the near infrared sources, and stores an average of the initial Optical Density values of the calibration standard for all of the near infrared sources. The computer also compares subsequent Optical Density values of the calibration standard for each of the near infrared emitting sources with the individual and average initial Optical Density values, and then compensates for Optical Density, variations between the subsequent and initial Optical Density measurements for each of the sources, so as to provide an analysis corrected for bias shift.

DETAILED DESCRIPTION OF PREFERRED EMBODIMENTS

Figure 1:
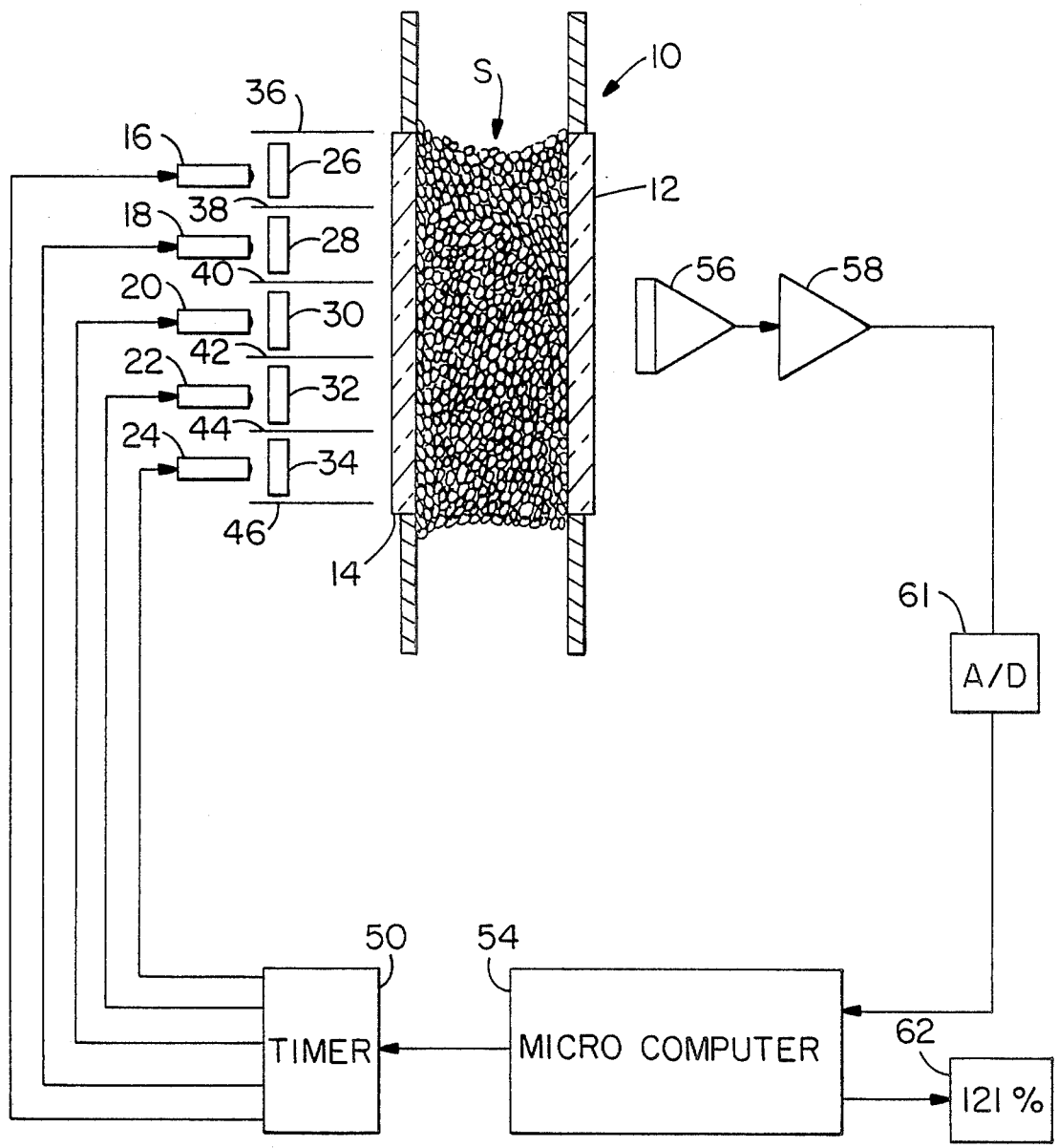
Figure 1 is a schematic diagram of a near infrared quantitative analysis instrument to which the present invention is applicable.

The present invention corrects bias shift in near infrared quantitative analysis instruments employing a plurality of near infrared emitting sources. One such instrument is schematically shown in FIG. 1, wherein a sample holding chamber 10 can be any form of suitable chamber having at least a portion thereof transparent to near infrared energy, such as windows 12 and 14. A sample S to be analyzed may be, for example, unground cereal grain. A sample is contained within the holding chamber 10 during measuring. Suitable gates (not shown) are positioned to put the sample in the chamber during measurement and to remove the sample from the chamber following the measurement.

A plurality of infrared emitting diodes (IRED's) 16, 18, 20, 22, and 24 are positioned so that when sequentially pulsed they will emit their illumination or infrared energy through individual narrow band pass filters 26, 28, 30, 32 and 34. Suitable IRED's are manufactured by General Electric, Model No. IN624. The combination of each IRED and its corresponding filter is referred to herein as a near infrared emitting source. For convenience, five IREDs and filters are shown, although the actual number used may be more or less than five. Preferably the number of IREDs used is 12. Suitable shields such as baffles 36, 38, 40, 42, 44, and 46 shield the individual IREDs and filters from other light sources. The beams from the individual IREDs may be focused together by suitable lens means (not shown). Each narrow band-pass filter yields one of the specified wavelengths required for the quantitative analysis. The temperature of the sample S may be sensed by a thermistor (not shown) which can be positioned within the holding chamber 10 in contact with the sample. A timer 50 is connected to the individual IRED's 16-24 to sequentially pulse them. A suitable timer is National Semiconductor Model No. NE555.

The optical energy transmitted through the sample S by the IREDs is quantitatively detected by a photovoltaic sensor 56. A suitable sensor is Silicon Detector Corporation Model No. SD444-11-21-251. The output of the sensor is amplified by an amplifier 58 and fed to an analog-to-digital converter 61 to convert the signal to digital form for entering into a micro-computer 54. The amplifier 58 can be a National Semiconductor Model LF355, the analog-to-digital converter 61 can be an Analog Devices Corporation Model AD574KD, and the micro-computer 54 can be an Intel 8085A system.

For further reference to the operation of the pulsed IREDs and to the use of narrow band-pass filters, see the above cited U.S Pat. Nos. 4,286,327 and 4,466,076, incorporated herein by reference.

Although five near infrared sources are shown for convenience in FIG. 1, the invention will be further described with reference to the near infrared analysis instrument having the preferred number of twelve IREDs and filters, mentioned above.

Figure 2:
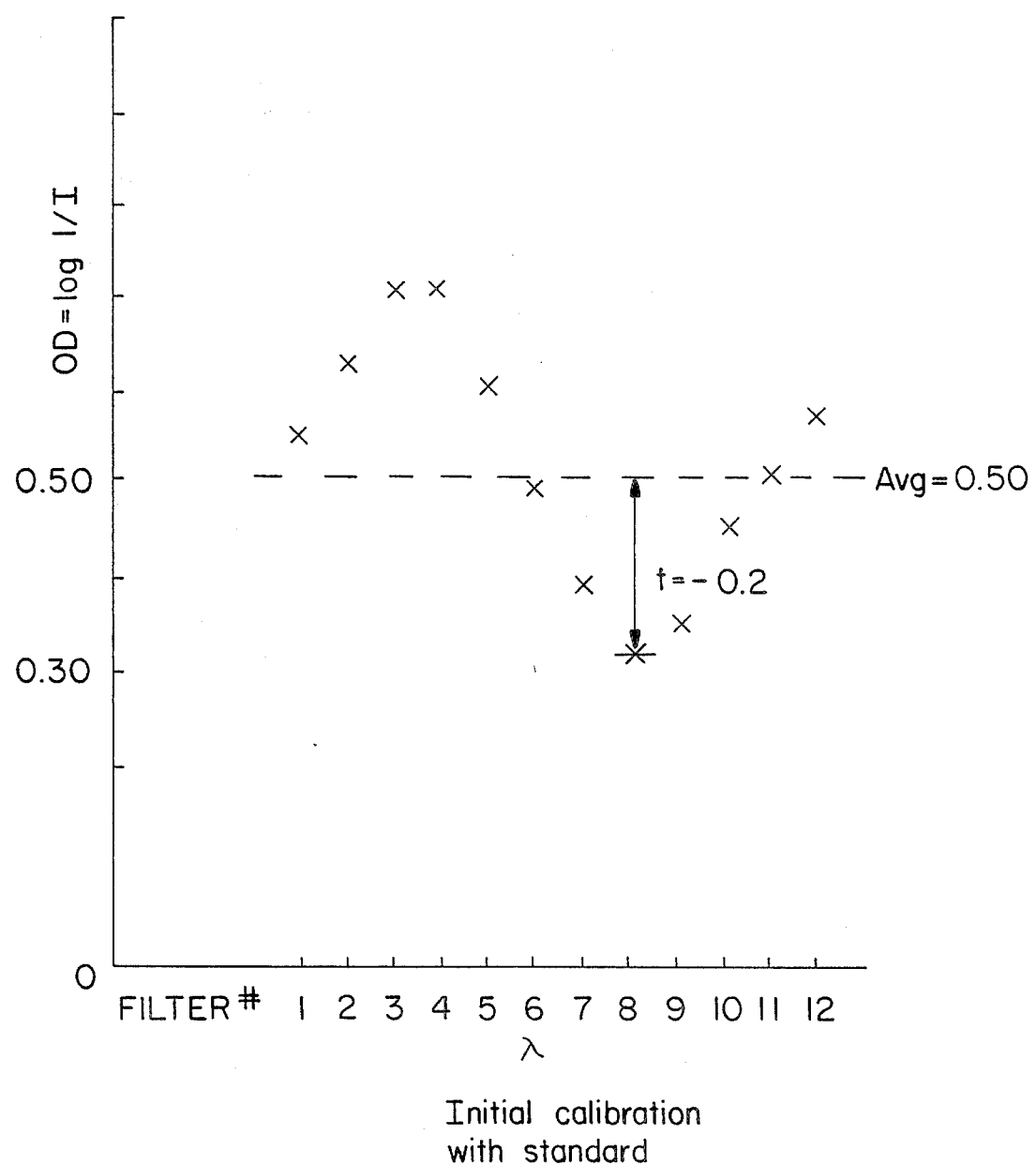
FIG. 2 is a graph illustrating sample absorbance values for each filter of an instrument as in FIG. 1, at the time of initial calibration.
Figure 5:
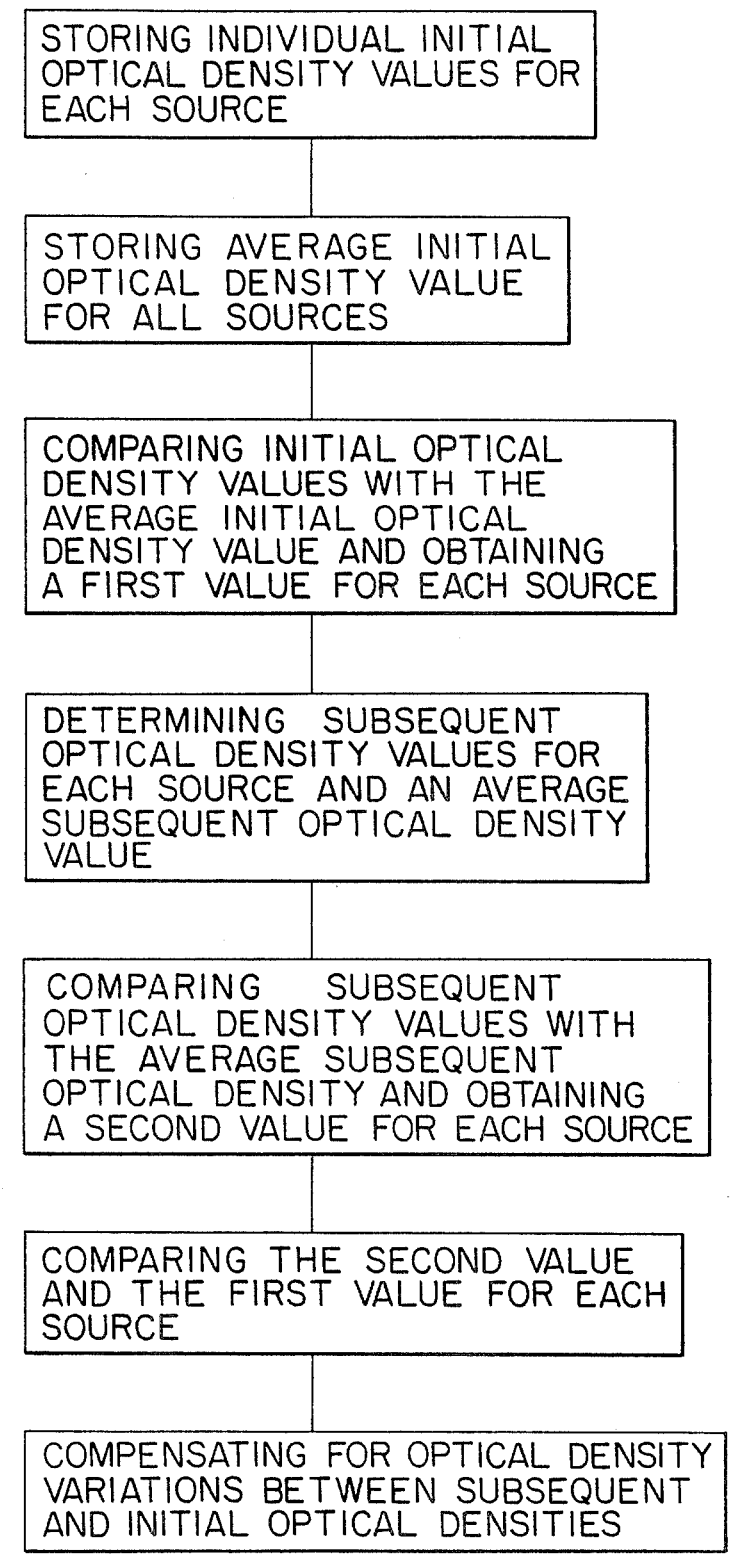
FIG. 5 is a flow diagram illustrating correcting for bias shift according to the present invention.

FIG. 2, shows Optical Density (OD)=log 1/I values of radiation received from each of 12 near-IR sources (i.e., 12 IREDs, each having a corresponding filter) during initial calibration of the instrument with a calibration standard. In the above equation, I is interactance and equal to Es/Er (Es =energy received from sample; Er =energy received from a reference). These initial OD values are obtained by transmitting optical energy from each of the 12 near-IR sources through an empty holding chamber, the calibration standard being air. According to the present invention, as illustrated in the flow diagram in FIG. 5, these initial OD values are stored in the computer 54 individually, and also combined to yield an average initial Optical Density value, which also is stored in the computer. Each initial OD value is then compared to the initial average value to obtain a "t" (true) value for each IRED/filter combination, which also is stored in the computer. The average initial or normalized Optical Density value of the calibration standard for all twelve of the near-IR sources, as shown in FIG. 2, is 0.50.

In this example, at the time of initial calibration, the Optical Density value of the calibration standard for radiation emitted by near-IR source No. 8 is 0.3, as shown in FIG. 2. Thus, the true (t) value for rear-IR source No. 8 is determined by comparing the OD value of source No. 8 to the average OD value for all twelve of the near-IR sources. Thus, source No. 8 has a "t" value of $0.3 - 0.5 = -0.2$.

Figure 3:
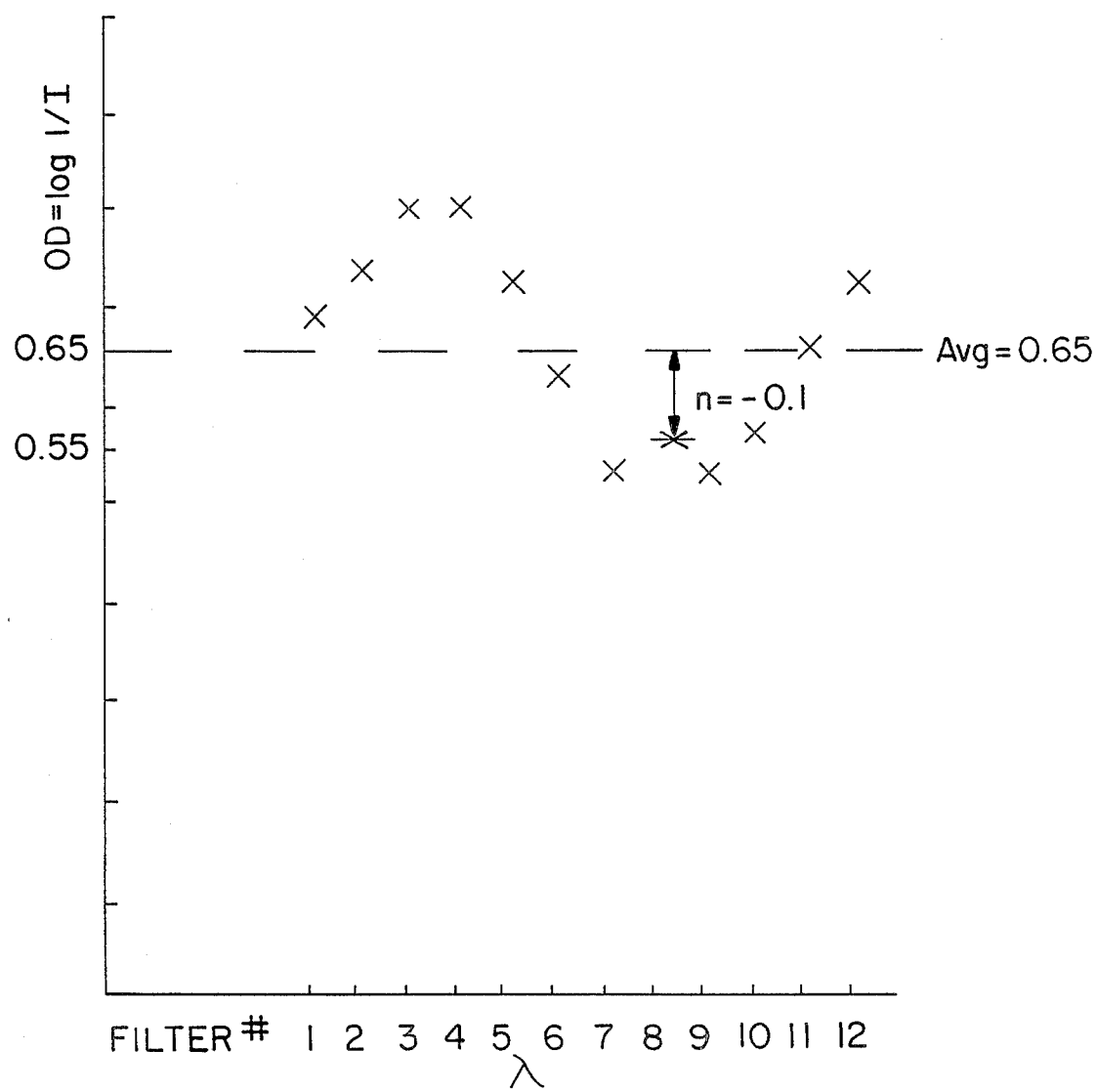
FIG. 3 is a graph exemplifying the effect of bias shift on absorption values for each filter of an instrument as in FIG. 1 after a period of time.
Figure 4:
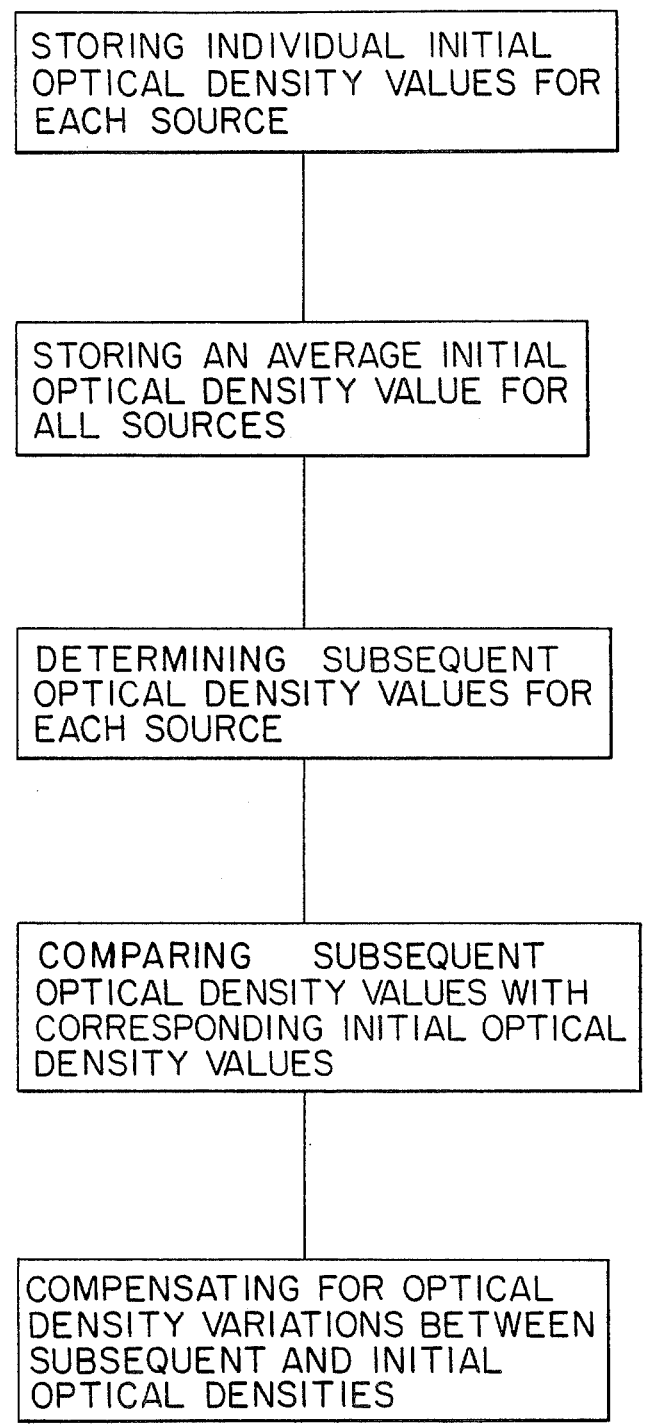
FIG. 4 is a flow diagram illustrating correcting for bias shift in the apparatus of the present invention.

FIG. 3, shows OD values during subsequent calibration with air as a standard for each of the twelve near-IR sources after a bias shift has occurred, such as might be attributable to wear or other factors which cause the readings to change. At this point, the average OD value for all twelve near-IR sources has changed to 0.65, as shown by the dotted line in FIG. 3. As compared to the new average OD value for all twelve near-IR sources, source No. 8 has an OD value of $-0.55$ and an n (now) value of $-0.1$.

In the present invention, the computer compensates for Optical Density variations between the subsequent and initial optical densities for each of the near-IR sources so as to provide an analysis corrected for bias shift. A formula that the computer can utilize to determine the percent protein in cereal grain in a near infrared instrument that corrects for bias shift according to the invention is as follows:

$$k^1{}_0 = k_o + f_1(n_1 - t_1) + f_2(n_2 - t_2) \ldots + f_{12}(n_{13} - t_{12})$$

where $k^1{}_0$ = corrected percent protein reading; $k_0$ = the uncorrected percent protein reading; each n value is the new OD value for a particular near IR source; each t time value is the true OD value for a particular near-IR source; and each f value is the "transfer function" for a particular near-IR source. The transfer function, which also may be termed a 37 weighting factor 38, expresses the percent contribution that the bias shift of a particular near-IR source is to the percent protein reading. In a near infrared analytical instrument wherein each IRED utilizes a dropping resistor (not shown), the transfer function may be determined experimentally by sequentially adding a small resistor in parallel to the dropping resistor of each IRED and then analyzing a test sample (e.g., grain) to determine the percent change.

The present invention thus provides a method and apparatus for correcting bias shift in near infrared quantitative analysis instruments that irradiate a sample with a plurality of near infrared emitting sources.

Since many modifications, variations, and changes in detail may be made to the described embodiment, it is intended that all matter in the foregoing description and shown in the accompanying drawings be interpreted as illustrative and not in a limiting sense.

What is claimed is;

1. An apparatus for near infrared quantitative analysis which corrects for bias shift, comprising:
   a) a plurality of near infrared emitting sources for transmitting near infrared energy through a sample
   b) sensor means for detecting near infrared energy transmitted through the sample, and providing a signal corresponding to optical density of the same for each of said near infrared emitting sources;
   c) a computer that is storing individual initial Optical Density values of a calibration standard for each of said near infrared emitting sources, which computer is also storing and average initial Optical Density value of said calibration standard for all of said near infrared emitting sources, said computer further comprising processor means for comparing subsequent Optical Density values of said calibration standard for each of said near infrared emitting sources with corresponding stored individual initial Optical Density values and the stored average initial Optical Density Value, and force compensating for Optical Density variations between the subsequent and initial Optical Densities based on said comparing for each of said near infrared emitting sources so as to provide an analysis corrected for bias shift.

2. The apparatus of claim 1 wherein each of said near infrared sources includes an infrared emitting diode and a corresponding optical narrow band-pass filter.

3. The apparatus of claim 1 wherein the calibration standard is air.

4. A method for correcting for bias shift in a near infrared quantitative analysis instruments that irradiate a sample with near infrared energy emitted from a plurality of near infrared emitting sources, comprising:
   a) storing individual initial Optical Density values of a calibration standard for each of said near infrared emitting sources;
   b) storing an average initial Optical Density value of said calibration standard for all of said near infrared emitting sources;
   c) determining subsequent Optical Density values of said calibration standard for each of said near infrared emitting sources;

d) comparing said subsequent Optical Density values for each of said near infrared emitting sources with corresponding stored individual initial Optical Density values and the stored average initial Optical Density value; and e) compensating for Optical Density variations between the subsequent and initial optical densities for each of said near infrared emitting sources so as to provide an analysis corrected for bias shift.

5. An apparatus for near infrared quantitative analysis which corrects for bias shift, comprising:

a) a plurality of near infrared emitting sources for transmitting near infrared energy through a sample;

(b) sensor means for detecting near infrared energy transmitted through the sample, and for providing a signal corresponding to Optical Density of the sample for each of said near infrared emitting sources;

c) a computer means for storing individual initial Optical Density values of a calibration standard for each of said near infrared emitting sources, said computer means also storing an average initial optical density value of said calibration standard for all of said near infrared emitting sources, said computer means further comprising means for comparing the individual initial Optical Density values for each said near infrared emitting sources with said average initial Optical Density value and obtaining a first value for each of said near infrared emitting sources, said computer means obtaining individual subsequent Optical density values of aid calibration standard for each of said near infrared emitting sources and an average subsequent Optical Density value of aid calibration standard for all said near infrared emitting sources, said computer means comprising means for comparing the individual subsequent Optical Density values for each of said near infrared emitting sources with said average subsequent Optical Density value and obtaining a second value for each aid second near infrared emitting sources, said computer means further comprising processor means for comparing said second value with said first value for each said near infrared emitting diode and for compensating for Optical Density variations between the subsequent and initial Optical Densities based on said comparing for each of said near infrared emitting sources so as to provide an analysis corrected for bias shift.

6. The apparatus of claim 1, wherein said processor means compares said second value with said first value for each of said near infrared emitting sources according to the following formula:

$$k^1{}_0 = k_0 + f_1(n_1 - t_1) + f_2(n_2 + t_2) \ldots + f_n(n_n - t_n)$$

where $k^1{}_0$ is a signal corrected for bias shift, $k_0$ is an uncorrected signal, each n value is the second value for each of said sources, each t value is the first value for each of said sources and each f value is a transfer function for each of said sources.

7. The apparatus of claim 5, wherein the calibration standard is air.

8. A method for correcting for bias shift in a near infrared quantitative analysis instrument that irradiates a sample with near infrared energy emitted from a plurality of near infrared emitting sources, comprising:

a) storing individual and initial Optical Density values of a calibration standard for each of said sources;

b) storing an average initial Optical Density value of said calibration standard for all of said sources;

c) comparing said individual initial Optical Density values of each of aid source with said average initial Optical Density value and obtaining a first value for each of said sources;

d) determining subsequent Optical Density values of said calibration standard for each of said sources and an average subsequent Optical Density value of said calibration standard for each of said sources;

e) comparing said subsequent Optical Density values of each said source with said average subsequent Optical Density value and obtaining a second value for each of said sources;

f) comparing said second values with said first values for each of said sources; and g) compensating for Optical Density variations between the subsequent and initial Optical Densities for each of said sources so as to provide analysis corrected for bias drift.

* * * * *